(12) United States Patent
Tholath et al.

(10) Patent No.: US 8,623,336 B2
(45) Date of Patent: Jan. 7, 2014

(54) TRANSPARENT XYLOGLUCAN/CHITOSAN GEL AND A PROCESS FOR THE PREPARATION THEREOF

(75) Inventors: Emilia Abraham Tholath, Trivandrum (IN); Kalyad Simi Ghandroth, Trivandrum (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/139,679

(22) PCT Filed: Mar. 31, 2009

(86) PCT No.: PCT/IN2009/000217
§ 371 (c)(1),
(2), (4) Date: Sep. 26, 2011

(87) PCT Pub. No.: WO2010/070655
PCT Pub. Date: Jun. 24, 2010

(65) Prior Publication Data
US 2012/0009132 A1    Jan. 12, 2012

(30) Foreign Application Priority Data
Dec. 15, 2008 (IN) .......................... 2830/DEL/2008

(51) Int. Cl.
*A61K 31/722* (2006.01)
*A61K 47/36* (2006.01)
*A23L 1/05* (2006.01)

(52) U.S. Cl.
USPC .............................. 424/59; 426/578; 426/658

(58) Field of Classification Search
None
See application file for complete search history.

(56) References Cited

U.S. PATENT DOCUMENTS

| 4,970,150 | A  | * | 11/1990 | Yaku et al. ..................... 435/101 |
| 6,197,318 | B1 | * | 3/2001 | Abe et al. ........................ 424/401 |
| 7,217,417 | B2 |  | 5/2007 | Knapp et al. |
| 2004/0182575 | A1 |  | 9/2004 | Reddy |
| 2006/0172000 | A1 |  | 8/2006 | Cullen |
| 2010/0233267 | A1 | * | 9/2010 | Chen et al. ..................... 424/488 |

FOREIGN PATENT DOCUMENTS

| JP | 10259118 |  | 9/1998 |
| JP | 10259118 | A * | 9/1998 |
| JP | 10259142 |  | 9/1998 |
| JP | 2001064668 |  | 3/2001 |
| JP | 2001278727 |  | 10/2001 |
| JP | 2006069952 |  | 3/2006 |
| RO | 0119951 |  | 10/1998 |
| WO | 2008065388 |  | 11/2007 |
| WO | WO 2008133847 | A1 * | 11/2008 |

OTHER PUBLICATIONS

Nishinari et al., Xyloglucan, Handbook of Hydrocolloids, pp. 247-267, 2000.*
Remington's Pharmaceutical Sciences 17th Edition, Edited by Alfonso R. Gennarom, p. 240, 1985.*
Zhou et al., Xyloglucan in cellulose modification, Cellulose, 14, p. 625-641, 2007.*
Dutta et al., Chitin and chitosan: Chemistry, properties and applications, Journal of Scientific & Industrial Research, vol. 63, pp. 20-31, 2004.*
Molinarolo et al., Sorption of Xyloglucan Onto Cellulose Fibers, The Institute of Paper Chemistry, pp. 1-91, 1989.*
Nitta et al. "Gelation of Xyloglucan by Addition of Epigallocatechin Gallate as Studied by Rheology and Differential Scanning Calorimetry", Biomacromolecules, vol. 5, No. 4, 2004, pp. 1206-1213.
Kim et al. "Synergistic Interaction of Xyloglucan and Xanthan Investigated by Rheology, Differential Scanning Calorimetry, and NMR", Biomacromolecules, vol. 7, No. 4, 2006, pp. 1223-1230.
Yamanaka et al. "Gelation of tamarind seed polysaccharide xyloglucan in the presence of ethanol", Food Hydrocolloids, 14, 2000, pp. 125-128.
Nitta et al. "Synergistic Gel Formation of Xyloglucan/Gellan Mixtures as Studied by Rheology, DSC, and Circular Dichroism", Biomacromolecules, vol. 4, No. 6, 2003, pp. 1654-1660.
Shirakawa et al. "Tailoring of xyloglucan properties using an enzyme", Food Hydrocolloids, 12, 1998, pp. 25-28.
Dave et al. "Liquid crystalline, rheological and thermal properties of konjac glucomannan", Polymer, vol. 39 No. 5, 1998, pp. 1139-1148.
Nishinari et al., "Hydrocolloid gels of polysaccharides and proteins", Current Opinion in Colloid & Interface Science, 5, 2000, pp. 195-201.
Zhang et al., "Immobilization of β-galactosidase on Tamarind Gum and Chitosan Composite Microspheres", Journal of Bioactive and Compatible Polymers, vol. 21, No. 5, Sep. 2006, pp. 415-432.
Tang et al., "Dialdehyde starch-crosslinked chitosan films and their antimicrobial effects", Journal of Polymer Science Part B: Polymer Physics, vol. 41, Issue 9, May 2003, pp. 993-997.

* cited by examiner

Primary Examiner — David J Blanchard
Assistant Examiner — John P Nguyen
(74) Attorney, Agent, or Firm — K&L Gates LLP (57) ABSTRACT

The present invention provides a transparent Xyloglucan/Chitosan gel and a process to prepare the same which comprises of extracting the xyloglucan from tamarind seed powder by a suitable solvent at a high temperature and precipitating the xyloglucan by alcohol and then modifying the xyloglucan to form dialdehyde and making a co-polymer with chitosan to form a thermo stable crystal clear, colourless gel which is stable at temperature −20 to 90. A transparent chitam gel and a process for the preparation thereof C and pH 3-7, having an average molecular weight of 4730 KDa and a viscosity of 4100 centi Poises at 28±2° C., not digested by digestive enzymes in humans and does not contribute to calorie intake can be used as a food ingredient, and supplement functional foods (nutritional care). This Xyloglucan/Chitosan gel has applications in the area of cosmetic and personal care products, as an ultraviolet protective agent or as a tissue adhesive which can be used, including haemostasis, wound sealing, tissue engineering or localised drug delivery as capsules & tablets.

10 Claims, 6 Drawing Sheets

TRANSPARENT XYLOGLUCAN/CHITOSAN GEL AND A PROCESS FOR THE PREPARATION THEREOF

FIELD OF THE INVENTION

The present invention relates to a novel transparent Chitam gel and a process for the preparation thereof. The present invention particularly relates to a crystal clear, colourless, nontoxic, biodegradable, biocompatible gel from xyloglucan and chitosan co-polymer which is herein after referred to as chitam gel. The invention also relates to an improved process for the preparation of the said non thermo reversible, gel using a copolymer of modified xyloglucan with chitosan. The process is simple, cost effective and can be scaled up. The gel can be used for a variety of applications, such as make-up cosmetic or basic cosmetic such as face wash, milky lotion, cream or foundation, with excellent elasticity and aging stability, giving refreshing feeling, free from stickiness and having excellent usability, as a ultraviolet protective agent or as a tissue adhesive which can be used, including haemostasis, wound sealing, tissue engineering or localised drug delivery as capsules & tablets and also can be used as a food ingredient, and supplement for metabolic disorders since it is not digested by the human digestive enzymes and yields zero calorie to the diet.

BACKGROUND OF THE INVENTION

Today's consumers in the cosmetic, food and beverage market are increasingly interested in healthy life styles, a trend which has produced a sky rocketing demand for health oriented products. Cosmetic and personal care products manufacturers claim that there is burgeoning trend for transparent products for instance those which use clear formulation techniques in their gels and emulsions. Pure xyloglucan extracted from tamarind seed as such does not form a gel; however, it is reported that it forms a thermoreversible gel in the presence of a large amount of alcohol or sugar or by the addition of a polyphenol such as epigallocatechin gallate. It was also reported that xyloglucan alone can form a gel if a part of the galactose is removed. The gel strength became greater with increasing removal ratio of galactose from xyloglucan. Xyloglucan along with xanthan or gellan or curdlan is reported to have synergistic interaction at low temperatures and results in an increase in the elastic moduli. The gelation scheme is different from that observed for an aqueous solution of enzymatically degraded xyloglucan which forms gel at a higher temperature. In the case of enzymatically degraded xyloglucan, the cross-linking domains are composed of aligned xyloglucan chains in the shape of flat plates, whereas no ordered structure was found for the cross-linking domains in the xyloglucan/ethanol system at lower temperatures. Xyloglucan undergoes thermo reversible gelation in the presence of ethanol. The cross-linking domain seems to be formed by random aggregation of xyloglucan chains due to poor solubility in ethanol. The analysis by time-resolved small-angle X-ray scattering has revealed that the complete dissolution of aggregates corresponds to the gel-sol transition. Here the cross-linking domain seems to be composed of random aggregates and has no ordered structure. Hence the gels which is crystal clear, colorless, not thermo reversible, non toxic, biodegradable, biocompatible and having an ordered structure and from renewable resources and hence, cost effective are in great demand globally.

Reference is made to Y. Nitta, Y. Fang, M. Takemasa, and K. Nishinar Nishinari, Biomacromolecules, 5, (2004), 1206-1213, wherein the interaction of tamarind seed xyloglucan and epigallocatechin gallate to induce a thermo reversible gelation was investigated and the draw backs are the gel formed was thermo reversible and was not transparent.

Yet another reference is made to Bo-Sook Kim, Makoto Takemasa, and Katsuyoshi Nishina, 'Synergistic Interaction of Xyloglucan and Xanthan Investigated by Rheology, Differential Scanning Calorimetry, and NMR', Biomacromolecules, 7, (2006), 1223-1230, wherein the synergistic interaction between tamarind seed xyloglucan and xanthan was found at low temperatures however the draw back is the gels are thermo-reversible.

Yet another reference is made to S. Yamanaka, Y. Yuguchi, H. Urakawa, K. Kajiwara, M. Shirakawa, K. Yamatoya, '*Gelation of tamarind seed polysaccharide xyloglucan in the presence of ethanol*', Food hydrocolloids, 14, (2000), 125-128. wherein the xyloglucan undergoes thermoreversible gelation in the presence of ethanol at lower temperatures the draw back is that the gels are thermoreversible.

Yet another reference is made to Yoko Nitta, Bo S. Kim, Katsuyoshi Nishinari, Mayumi Shirakawa, Kazuhiko Yamatoya, Toshio Oomoto, and Iwao Asai, Synergistic Gel Formation of Xyloglucan/Gellan 'Mixtures as Studied by Rheology, DSC, and Circular Dichroism', Biomacromolecules, 4, (2003), 1654-1660. wherein the gelation behavior of mixtures of tamarind seed xyloglucan and sodium form gellan was investigated. The synergistic interaction of helix-forming polysaccharides and the storage and loss shear moduli, G' and G", of the mixtures showed that it is a thermoreversible gel and the draw back is that the gels are thermoreversible.

Yet another reference is made to Mayumi Shirakawa, Kazuhiko Yamatoya, Katsuyoshi Nishinari, '*Tailoring of xyloglucan properties using an enzyme*', Food Hydrocolloids, 12, (1998), 25-28. wherein the by removing 35% of the galactose residues from xyloglucan of tamarind seed using fungal β-galactosidase, it had the unique property of forming a gel on heating and reverting to a sol state on cooling. The gel strength at a higher temperature was greater than that at a lower temperature. The phase transition between sol and gel was reversible. Gelation was believed to be induced by the association of main chains by hydrophobic binding and the draw back in this type of gels are they are temperature dependent.

Yet another reference is made to Vipul Dave, Mihir Sheth, Stephen P. McCarthy, Jo Ann Ratio, David L. Kaplan, '*Liquid crystalline, rheological and thermal properties of konjac glucomannan* Galactomannan', Polymer, 39, (1998), 1139-1148, wherein the addition of coagulant through deacetylation, and the gelation is promoted by heating with curdlan to form either a thermo-reversible gel or a thermo-irreversible gel at relatively lower or higher heating temperatures, and the draw back is both are not xyloglucans.

Yet another reference is made to K Nishinari, H Zhang, S Ikeda, '*Hydrocolloid gels of polysaccharides and proteins*', Current Opinion in Colloid & Interface. Science, 5, (2000), 195-201., wherein the Locust bean gum (LBG) forms a gel by freeze/thaw cycling and the gelation rate becomes a maximum at −5° C. and LBG gels exhibit true gel-like character and the draw back is that both are not xyloglucans.

Yet another reference is made to Yano yoshihiro, Shimada kunio, Fukuda nobuo, 'Aroma-keeping agent containing polysaccharide having hydrophobic group', JP2001064668A2, 2001: wherein a cosmetic gel composed of a polysaccharide derivative containing a hydrophobic group as a aroma retention agent is described and the draw back is that they are not xyloglucans.

Yet another reference is made to Abe koji, Miyahara reiji, Nanba tomiyuki; Uehara keiichi, 'Cosmetics—contains xyloglucan and viscous polysaccharide', JP10259118A2, 1998, wherein the cosmetic is prepared by formulating a xyloglucan and thickening polysaccharides and a sugar-based surfactant in combination, and the draw back is that they are not xyloglucan gels.

Yet another reference is made to Abe koji, Miyahara reiji, Nanba tomiyuki; Uehara keiichi, 'Cosmetic for skin—contains xyloglucan and ultraviolet ray shielding agent', JP10259142A2, 1998: wherein the cosmetic contains xyloglucan and an ultraviolet protective agent, and the draw back is that they are not thermostable transparent gels.

Yet another reference is made to Mori satoru, Asahi kasei corp, cosmetics, an aqueous solution of which with a solid content of 10% has a pH of 5-8, comprises n-acyl glutamic acid salt and xylo glucan, JP 2001278727A2, 2001: wherein the cosmetic comprises an n-acyl glutamate and xyloglucan and is adjusted to pH 5 to 8 to obtain a cosmetic having low irritation, slight stickiness after use, a proper viscosity, not causing precipitation, cloudiness, etc. even at a low temperature an excellent low-temperature stability and the draw back is that they are not transparent stable gels.

Yet another reference is made to Shibata saori, Nippon shikizai inc, 'Gel-form cosmetics useful as make-up cosmetic or basic cosmetic such as face wash, milky lotion, cream or foundation, contain xyloglucan, lower alcohol and powder-form component', JP2006069952A2, 2006: wherein the gel is produced by compounding xyloglucan with a lower alcohol and powder and the draw back is that they are not transparent sturdy gels.

Yet another reference is made to Walker, Greg WO08065388A2: 2008, wherein the method for the formation of the biogel which is a tissue adhesive is described and the draw back is that they are not xyloglucan gels.

Yet another reference is made to Bucevschi mircea dan, Caloianu maria, Musteata bogdan, Alupei cornel, Coltmonica, Iordachel radu, Moldovan lucia, Iordachel catalin, Topolniceanu florin, 'Permeable biogel based on collagen fiber, comprises a brain disease pharmaceutical based on modification by ethyl acrylate and maleic anhydride', RO0119951B1: wherein a permeable biogel based on collagen fibers, meant for adjusting the flow of biological fluids and glandular secretions, in treating some cerebral and endocrine affections are made but they are not transparent, stable xyloglucan gels.

Yet another reference is made to Knapp, Barry Disalvo, Ronald, 'Gel-based cosmetic and wound-healing formulation and method', U.S. Pat. No. 7,217,417, 2007. wherein a gel-based cosmetic and wound-healing formulations, comprises of live yeast cell extract, pigment, and a gel and the draw back is that it is not a transparent, stable xyloglucan gel.

Thus, keeping in view the drawbacks of the hitherto known prior art, the inventors realized that there exists a dire need to develop a transparent gel, which is non toxic and colourless. Also the gel could be made from easily and abundantly available raw material which is renewable in nature.

OBJECTIVES OF THE INVENTION

The main object of the present invention is therefore to provide a novel transparent chitam gel which is a copolymer of modified xyloglucan and chitosan.

Another object of the present invention is to provide a process for the preparation of a gel which is non toxic and colourless and from renewable resource and is abundantly available.

Yet another object is to provide a process wherein modified xyloglucan is prepared by periodate oxidation to form xyloglucan dialdehyde.

Yet another object is to provide a process wherein the transparent chitam gel is stable at higher temperature and neutral to acidic conditions.

Yet another object is to provide a process wherein the transparent chitam gel is not digested by digestive enzymes in humans and does not contribute to calorie intake.

Yet another object is to provide a used for cosmetic, pharmaceutical, and functional foods.

Yet another object is to provide a chitam gel as a carrier of natural or synthetic medicines, perfumes, flavors, nutrients, colours, UV retardants.

The various objects of the invention as stated above are met by employing a renewable raw material, the cost naturally comes down due to easy preparation of the gel.

SUMMARY OF THE INVENTION

The present invention provides a novel transparent Chitam gel and a process for the preparation thereof, which comprises of extracting the xyloglucan from tamarind seed powder by a suitable solvent at an acidic pH and at a high temperature and precipitating it by alcohol and then modifying the xyloglucan to form dialdehyde and making a co polymer with chitosan to form a thermo stable crystal clear, colourless gel.

Accordingly, the present invention provides transparent chitam gel represented by formula 1, wherein it comprises:
[a] a xyloglucan, and
[b] chitosan
wherein the ratio of [a]:[b] is in the range of 1 to 6:1 to 8 by weight of the polymer.

Accordingly, the present invention provides transparent chitam gel represented by formula 1, wherein it comprises:
[a] a xyloglucan, and
[b] chitosan
wherein the ratio of [a]:[b] is in the range of 1 to 6:1 to 8 by weight of the polymer.

n-21049
m-10401

The invention further provides a process for the preparation of the said chitam gel, wherein the steps comprising:
[a] preparing the tamarind slurry by dissolving the coarsely powdered tamarind in water wherein the ratio of tamarind powder to water is in the range of 1 to 10:10 to 20 at pH of 2 to 10 preferably 4 to 8;
[b] heating the slurry as obtained in step (a) at 10 to 100 degree. C preferably 40 to 80 degree C. followed by cooling to a temperature of 25 to 33 degree C. and precipitating it with alcoholic solvents like benzyl alcohol, Isopropanol, isobutanol, ethanol, methanol, Butanol etc. to obtain xyloglucan;

[c] drying the precipitated xyloglucan as obtained in step (b) under vacuum or freeze dried to obtain powder;

[d] dispersing the powdered xyloglucan as obtained in step [c] in water or any other solvents selected from DMSO, DMF, THF, dichloromethane, hexane, benzene, acetone acetic acid, formic acid etc. at a pH in the range of 7 to 14 to obtain a mixture;

[e] stirring the mixture as formed in step (d) with oxidative reagents selected from nitric acid, nitrous oxide, cerium compounds, perchlorate, periodate; permanganate etc at a temperature of 2 to 10 degree C. for 1 to 15 hours;

[f] terminating the reaction of step [e] by adding 1 to 10 ml of diols such as propylene glycol, ethylene glycol, or any other diols and purifying the liquid product by method such as dialysis or column chromatoghraphy to obtain xyloglucan dialdehyde;

[g] mixing the xyloglucan dialdehyde as obtained in step (f) with 1 to 10% chitosan at a pH in the range of 1 to 7;

[h] stirring, the mixture as obtained in step (g) for 1 to 5 min to obtain the desired transparent chitam gel.

In an embodiment of the present invention the xyloglucan is either naturally occurring or synthetically prepared.

In another embodiment of the present invention the xyloglucan is extracted from the seed powder of tamarind (tamarindus indica) jaloba (hymenacea courbaril), detarium gum, atzelia Africana, preferably from tamarind.

In another embodiment of the present invention the gel is useful in cosmetics, health care & hygiene, food processing, diet beverages and pharmaceutical applications.

In another embodiment of the present invention the gel has negligible calorific value so that it can be used for formulations of diet beverages, jams, jellies, marmalades, ice creams, sauces.

In another embodiment of the present invention the prepared gel exhibits the following characteristics:
 i. molecular weight 4730 KDa
 ii. stability at pH 3.0-8.0
 iii. color less, transparent gel
 iv. viscosity of 4100 centi Poises at 28±2° C.
 v. very good storage stablity between temperature −20 to 90° C.
 vi. do not decompose on prolonged exposure to sun light and
 vii. do not decompose for exposure to ultra violet rays.

In another embodiment of the present invention the gel is stable to exposure to ultraviolet rays in the time range of 2-4 hr and to sun light for 5-8 days.

In another embodiment of the present invention is provided a process for the preparation of the chitam gel.

In another embodiment of the present invention the pH at which the tamarind slurry is prepared is either 2 to 6.5, 6.5 to 7.5 or 7.5 to 10.

In another embodiment of the present invention the temperature for extracting xyloglucan from tamarind seed is preferably 80 to 100 degree C.

In another embodiment of the present invention the solution is acidified to pH 2 to 5 by citric acid, tartaric acid or lactic acid.

In another embodiment of the present invention the precipitated xyloglucan was modified by oxidation or reduction or derivatisation, to form dialdehyde, preferably by oxidation with reagents selected from hydrogen peroxide, potassium periodate, sodium periodate, at a temperature in the range of 2 to 10 degree C. with residence time of 4 to 10 h.

In another embodiment of the present invention the xyloglucan is modified to dialdehyde by oxidation with sodium periodate at a temperature of 4 degree C. for 6 to 10 hours.

In another embodiment of the present invention the xyloglucan is extracted from the tamarind seeds by solvent which is water.

In yet another embodiment the solvent is water having a pH of 3.0, temperature of 10-50° C. and an extract of xyloglucan was prepared.

In yet another embodiment of the invention, the acid was selected from the group comprising of oxalic acid and citric acid.

In yet another embodiment of the invention, the acid comprises of citric acid.

In yet another embodiment of the invention, the oxidation is done by peroxides or periodates.

Figure 1:
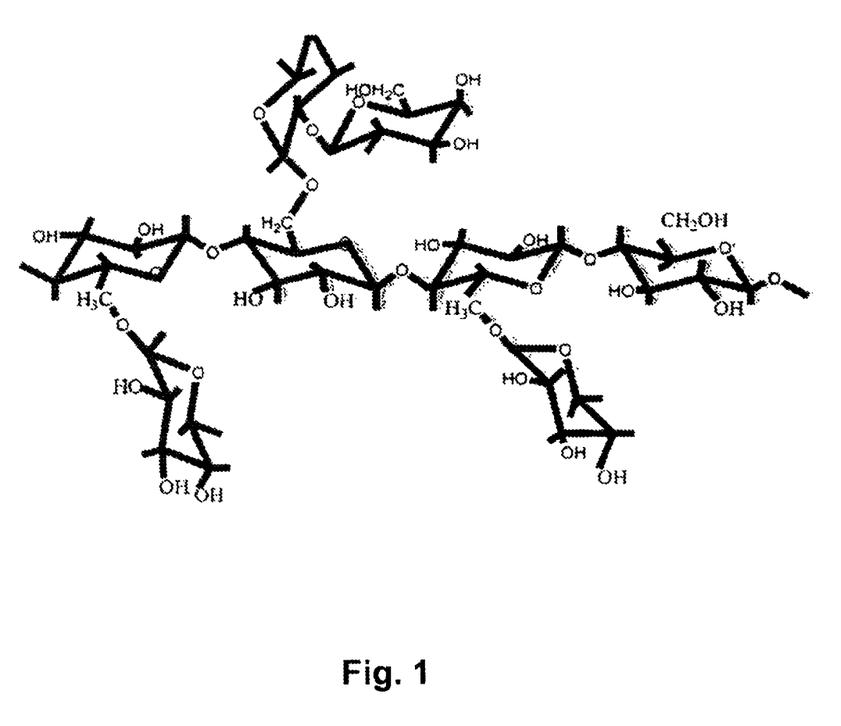
FIG. 1 represents the structure of xyloglucan.
Figure 2:
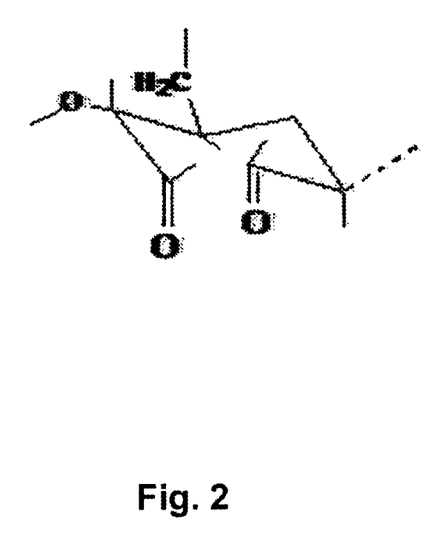
FIG. 2 is a perspective view of the structure of dialdehyde of xyloglucan.
Figure 3:
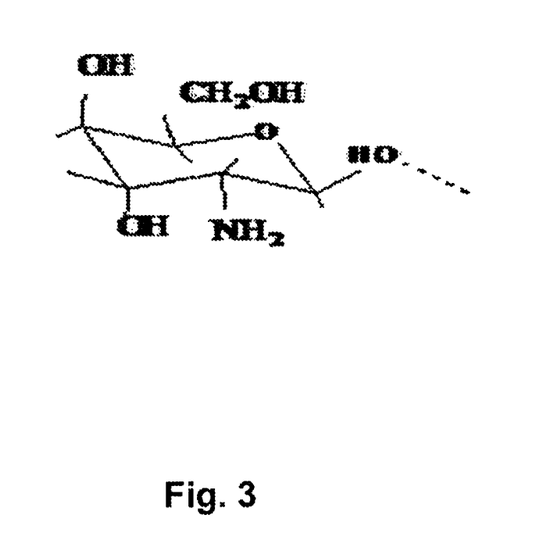
FIG. 3 represents the structure of chitosan.
Figure 4:
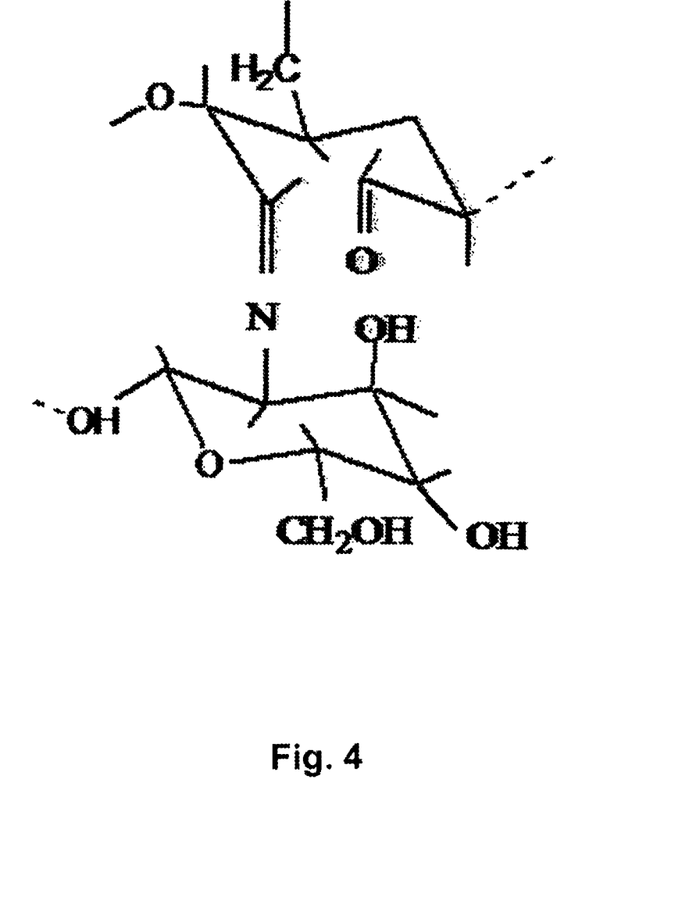
FIG. 4 shows the basic structure of the copolymer Chitam gel.
Figure 5:
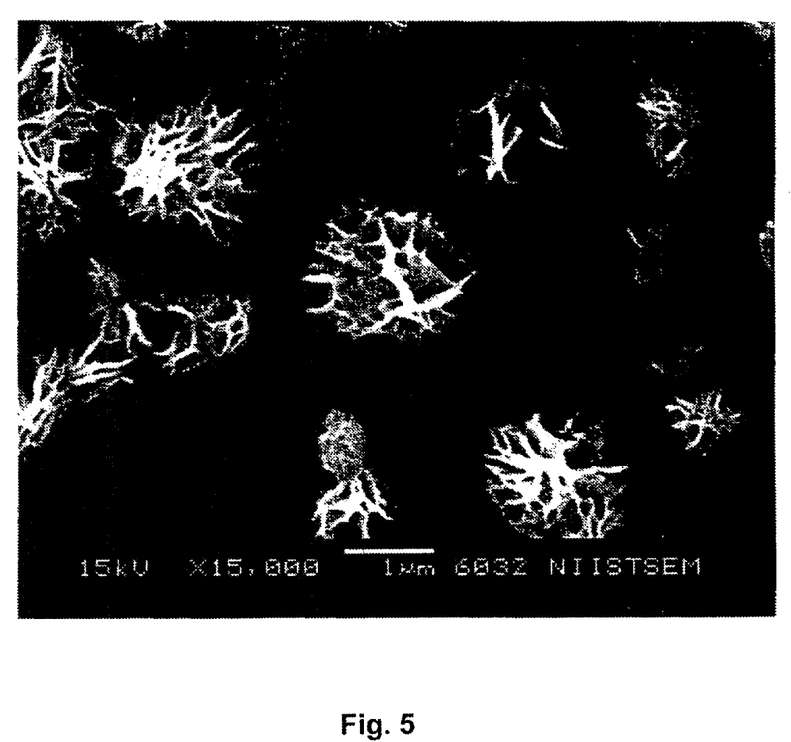
FIG. 5 shows the surface morphology of the Chitam gel coated with gold and seen under scanning electron microscope (SEM) at 15 KV.
Figure 6:
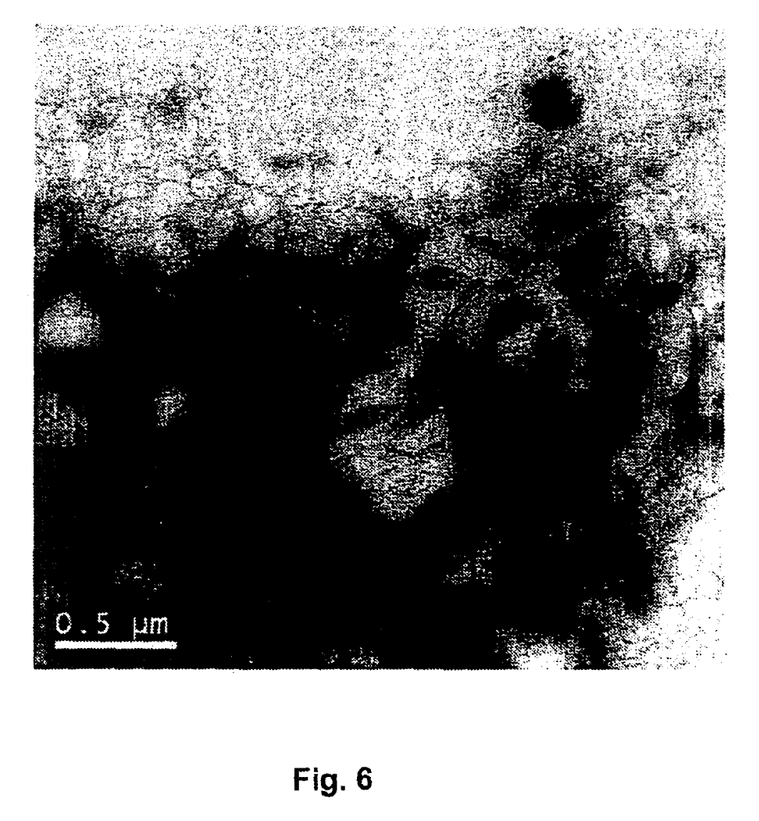
FIG. 6 shows structure of the gel by Transmission electron microscopy (TEM) at 100 KV.

In yet another embodiment of the present invention the dialdehyde xyloglucan is copolymerized with another naturally occurring polymers, specifically chitosan, to form formula of FIG. 1 a chitam gel, with a ratio of 1:1, 1:2, 1:3, 1:4. 2:1, preferably with the ratio of 1:3 by wt, at temperature range of 25 to 33 degree C. with a yield range of 90-98%, with bare minimum wastage.

In still another embodiment of the present invention the resultant to cross linked copolymer forms a crystal clear transparent colorless gel having good thermal and rheological properties.

BRIEF DESCRIPTION OF THE DRAWINGS

In the drawings accompanying the specification.

DETAILED DESCRIPTION OF INVENTION

The product as provided by the process of the present invention is a crystal clear Chitam gel which is a copolymer of two naturally occurring polysaccharides. The coarsely powdered tamarind powder was made into slurry with water of acidic or alkaline pH, heated to 10 to 100 degree. C preferably 40 to 80 degree C., cooled and precipitated with suitable solvents such as ethanol, methanol, benzyl alcohol, Isopropanol, isobutanol, n-butanol, etc in a concentration of 10 to 100% (v/v). The precipitated xyloglucan was dried under vacuum or freeze dried. Powdered xyloglucan was dispersed in water or any other solvents such as DMSO, DMF, THF, dichloromethane, hexane, benzene, acetone acetic acid, formic acid etc under alkaline conditions. Stirred the above reaction mixture with any of the oxidative reagents such as hydrogen peroxide, potassium periodate, sodium periodate at a temperature 2 to 10 degree C. for 1 to 15 h. Reaction was stopped by adding 1 ml ethylene glycol. The product formed was purified by any method such as dialysis or column chromatography. Pure oxidised sample was mixed with 1 to 10% chitosan in acidic medium and was stirred for 1 to 5 minutes to form cross links. Consequently, a clear chitam gel was obtained. About 1 gram dry weight raw material gives 100 gram wet, clear and sturdy gel.

The following examples are given by way of illustration and therefore should not be construed to limit the scope of the present invention.

EXAMPLES

The following examples describes the process for the preparation of xyloglucan from Tamarind powder

Example 1

Coarsely ground Tamarind kernel powder was made into a slurry with water in the ratio 1:5 at 28 degree C. This slurry was added to boiling water which was slightly alkaline. Boiled and kept it some time to solubilize the xyloglucan. Precipitated the xyloglucan with 70% ethanol. The precipitate was separated by centrifugation to get pure xyloglucan.

Example 2

Tamarind kernel powder was made into slurry with water at 28 degree C. This slurry was added to boiling water in the ratio 1:5 which was neutral. Boiled and kept it for some time. Precipitated the xyloglucan with alcohol.

Example 3

Tamarind kernel powder was made into slurry with water in the ratio 1:10 at 28 degree C. This slurry was added to boiling water which was acidic. Boiled and kept it.

The following examples describes the process for the preparation of dialdehyde xyloglucan

Example 4

0.5 g xyloglucan was suspended in water. Added slowly 1 g of hydrogen peroxide dissolved in 5 ml water. Reaction was continued for 6 h at 2 degree C. Reaction was stopped by adding 1 ml ethylene glycol. The product was dialyzed against distilled water for 12 hour.

Example 5

0.5 g xyloglucan was suspended in water. Added slowly 1 g sodium periodate dissolved in 5 ml water. Reaction was continued for 6 h at 2 degree C. Reaction was stopped by adding 1 ml ethylene glycol. The product was dialyzed against distilled water for 12 hour.

Example 6

0.5 g xyloglucan was suspended in water. Added slowly 1 g potassium periodate dissolved in 5 ml water. Reaction was continued for 6 h at 2 degree. C. Reaction was stopped by adding 1 ml ethylene glycol. The product was dialyzed against distilled water for 12 hour.

Example 7

1 g xyloglucan was suspended in water. Added slowly 1 g potassium periodate dissolved in 5 ml water. Reaction was continued for 10 h at 2 degree. C. Reaction was stopped by adding 1 ml ethylene glycol. The product was dialyzed against distilled water for 12 hour.

Example 8

1 g xyloglucan was suspended in water. Added slowly 1 g potassium periodate dissolved in 5 ml water. Reaction was continued for 12 h at 2 degree C. Reaction was stopped by adding 1 ml ethylene glycol. The product was dialyzed against distilled water for 12 hour.

The following examples describes the process for the preparation of Chitam gel

Example 9

1% chitosan in 1% acetic acid was prepared and 30 ml mixed with 10 ml of dialdehyde xyloglucan in appropriate proportion and allowed to cross link. 40 gm of transparent gel was obtained.

Example 10

2% chitosan in 1% acetic acid was prepared and mixed with 1% dialdehyde xyloglucan with equal volume proportion. A transparent gel was obtained at room temperature. 10 gm of raw material produced 1 kg of transparent gel.

Example 11

Preparation of Chitam gel as sunscreen chitam gel with homosalate was prepared as sunscreen and found to be stable under UV light of 256 nm range for 4 hours.

Example 12

To 50 grams of chitam gel food grade anthocyanins, are added for producing violet color, and aspartame, grape flavor and citric acid to get a zero calorie grape jellies, alternatively edible orange color is added along with citric acid, orange flavor, artificial sweetener and finely sliced orange peel to get zero calorie orange marmalade.

ADVANTAGES OF THE INVENTION

1. A Crystal clear nontoxic chitam gel from renewable resources is obtained.
2. The chitam gel is obtained in high yield since 10 gm raw material produces 1 Kg gel, with 100 fold yield and hence cost effective:
3. The chitam gel is tested to be thermostable from −20 to 90 degree C.
4. Zero calorie gel useful as a diet replacement, especially for diabetic patients can be incorporated on beverages, Jam, jellies, marmalades, to give the desired viscosity, gel characteristics and mouth feel compatible with edible colors, flavors and artificial sweeteners.
5. Very stable at acidic to neutral pH of 3.0 to 7.0 and hence can be used as a vehicle for drugs in oral, topical, or wound healing patches.
6. The chitam gel is easy to handle and hygienic and nontoxic.
7. No need for heat or long periods of stirring for the gel preparation since the gel is formed at room temperature and at atmospheric pressure; hence costly processing equipments are not necessary.
8. The desired final product viscosity can be tailor made from the chitam gel either modifying the percentage of xyloglucan, chitosan ratio or by diluting with suitable media.

We claim:

1. A process for the preparation of a gel having a structure of formula 1, comprising xyloglucan, and chitosan in the ratio of 1 to 6: 1 to 8 by weight, comprising the steps of:

FORMULA 1 n-21049
m-10401

[a] preparing a slurry by dissolving a xyloglucan source in water wherein the ratio of xyloglucan source to water is in the range of 1 to 10: 10 to 20 at a pH of 2 to 10;

[b] heating the slurry as obtained in step [a] at 40 to 80 degrees C. followed by cooling to a temperature of 25 to 33 degrees C. and precipitating the slurry with an alcoholic solvent selected from the group consisting of benzyl alcohol, isopropanol, isobutanol, ethanol, methanol, and n-butanol to obtain xyloglucan;

[c] drying the precipitated xyloglucan as obtained in step [b] under vacuum or freeze dried to obtain powder;

[d] dispersing the powdered xyloglucan as obtained in step [c] in water or a solvent selected from the group consisting of DMSO, DMF, THF, dichloromethane, hexane, benzene, acetone acetic acid, and formic acid at a pH in the range of 7 to 14 to obtain a mixture;

[e] stirring the mixture as formed in step [d] with an oxidative reagent selected from the group consisting of nitric acid, nitrous oxide, cerium compounds, perchlorate, periodate, peroxide, and permanganate at a temperature of 2 to 10 degrees C. for 1 to 15 hours;

[f] terminating the reaction of step [e] by adding 1 to 10 ml of a diol and purifying the liquid product by method such as dialysis or column chromatography to obtain pure oxidized sample;

[g] mixing the pure oxidized sample as obtained in step [f] with 1 to 10% chitosan at a pH in the range of 1 to 7;

[h] stirring the mixture as obtained in step [g] for 1 to 5 min to obtain a clear transparent chitam gel.

2. A process of claim 1, wherein in step [a] the pH is selected from the group consisting of 2 to 6.5, 6.5 to 7.5 or 7.5 to 10.

3. A process of claim 1, wherein in step [e] the xyloglucan mixture is modified by oxidation, to form dialdehyde, by a reagent selected from hydrogen peroxide, potassium periodate, and sodium periodate, at a temperature in the range of 2 to 10 degrees, C. with residence time of 4 to 10 h.

4. A process of claim 3, wherein the xyloglucan mixture is modified to dialdehyde by oxidation with sodium periodate at a temperature of 4 degrees C. for 6 to 10 hours.

5. A process of claim 1 wherein the gel so obtained has general formula 1:

FORMULA 1 n-21049
m-10401

6. A process of claim 1, wherein the xyloglucan source is a material selected from the powdered seed of tamarind (tamarindus indica), jaloba (hymenacea courbaril), detarium gum and atzelia Africana.

7. A process of claim 1, wherein the gel obtained is useful in cosmetics, health care & hygiene, food processing, diet beverages and pharmaceutical applications.

8. A process of claim 1, wherein the gel obtained has negligible calorific value.

9. A process of claim 1, wherein in step [a] the pH is 4 to 8.

10. A process of claim 1, wherein in step [f] the diol is propylate glycol or ethylene glycol.

* * * * *